United States Patent [19]

Ciaudelli et al.

[11] 4,069,309
[45] Jan. 17, 1978

[54] CATIONIC SKIN SUBSTANTIVE SUNSCREEN COMPOSITION AND METHOD

[75] Inventors: Joseph P. Ciaudelli, Ramsey; Gerhart Karg, Pompton Lakes, both of N.J.

[73] Assignee: Avon Products, Inc., Suffern, N.Y.

[21] Appl. No.: 290,327

[22] Filed: Sept. 19, 1972

[51] Int. Cl.$^2$ .................... A61K 31/42; C07C 101/00
[52] U.S. Cl. ........................ 424/47; 424/60; 560/49; 560/48
[58] Field of Search .................... 424/60, 47; 260/472

[56] References Cited

U.S. PATENT DOCUMENTS

| | | | |
|---|---|---|---|
| 2,596,156 | 5/1952 | Krimmel | 260/472 X |
| 2,620,352 | 12/1952 | Beatty | 260/472 |
| 2,623,045 | 12/1952 | Schlesinger et al. | 260/472 X |
| 2,717,905 | 9/1955 | Ziegler | 260/472 |
| 2,726,259 | 12/1955 | Simonoff | 260/472 |
| 2,853,423 | 9/1958 | La Via | 424/60 X |
| 2,890,979 | 6/1959 | Korner | 260/472 X |
| 3,506,758 | 4/1970 | Epstein | 424/60 |

OTHER PUBLICATIONS

Bird, Journal of American Pharmaceutical Assoc. Sci. Ed., 1942, vol. 31, pp. 151–154.
Jensen et al., Acta Chemica Scandinavica 2, (1948), pp. 381–384.

*Primary Examiner*—Dale R. Ore
*Attorney, Agent, or Firm*—Pennie & Edmonds

[57] ABSTRACT

Sunscreening compositions and methods for using the same to protect human skin from erythema producing ultraviolet radiation by applying to the skin a cosmetic carrier composition containing an effective amount to substantially prevent erythema of a cationic para-amino benzoate ester of a substituted amino alkanol. Sunscreening compositions containing cationic para-amino benzoates when applied to the skin have been found to be substantially uneffected by moisture from perspiration or swimming and are, therefore, substantive in form.

7 Claims, No Drawings

CATIONIC SKIN SUBSTANTIVE SUNSCREEN COMPOSITION AND METHOD

BACKGROUND OF THE INVENTION

It is well known that exposure to the sun, sunlamps, or other tanning means to which individuals subject themselves also exposes such individuals to ultraviolet radiations between the wavelengths of about 280 millimicrons to about 320 millimicrons which are responsible for distressing burning and reddening (erythema) which is suffered by overexposure to such tanning means. In order to permit tanning without burning so-called sunscreening compositions have been made commercially available to diminish or avoid discomforts and dangers of erythema which may be produced. These compositions are adapted to be applied to the body areas which are to be exposed for tanning and their formulations generally contain a compound which can absorb ultraviolet radiation in the range of from about 280 to 320 millimicrons and thus alleviate the problems of erythema.

As is known, an effective sunscreening preparation essentially performs two functions. The first and most important is to protect the user from burning, blistering and injurious effects of prolonged exposure to sunlight. The second function is to permit the most rapid possible development of the skin pigmentation or tanning. As noted above, the erythemal range from which protection is sought lies between about 280 and 320 millimicron units. It is generally agreed that effective, relatively rapid tanning, without painful erythema results from exposure of the skin to radiation from about 320 to about 420 millimicron units. An effective suntan preparation is thus one which selectively absorbs or screens the erythema rays and permits transmission of the tanning rays above the 320 millimicron range.

It has been known that various aminobenzoic acid derivatives have sunscreening properties. These include the derivatives of ortho and para-aminobenzoic acid such as the dimethylaminobenzoic acids which have been used in the past in suntanning preparations. It is also known that esters of ortho- and para-aminobenzoic acid, such as the methyl, ethyl or propyl benzoates, as well as those esters from higher alkyl alcohols have valuable sunscreening effects. Such compounds, while having desirable properties, have been found not ideally suited for the purpose intended. They lack one or more of such desirable characteristics as insolubility in water, nonstaining of fabrics, stability on storage, stability on exposure to ultraviolet or visible radiation, resistance to air oxidation, solubility in cosmetic carriers at low temperatures, such as room temperature, and substantiveness to the skin.

The majority of the sunscreening compounds known heretofore lack the essential characteristic of being substantive to the skin. The majority of compounds, when topically applied in the various known forms, have been easily removed from the skin by salt or fresh water or through the action of perspiration of the user. In as much as sunscreening compositions are generally used in hot weather and at beaches and water facilities where people enjoy bathing activities, such compositions which are removed by water have limited effectiveness. Even where artificially induced rays, such as by commercially available sunlamps, are used the heat causes the user to perspire which, in turn, washes away the sunscreening agents.

SUMMARY OF THE INVENTION

It has now been found that sunscreening formulations which are useful in absorbing the erythema-producing rays of the sun are formed by the inclusion in a cosmetic carrier composition an effective amount to prevent erythema of cationic aminobenzoates selected from the group having the general formula:

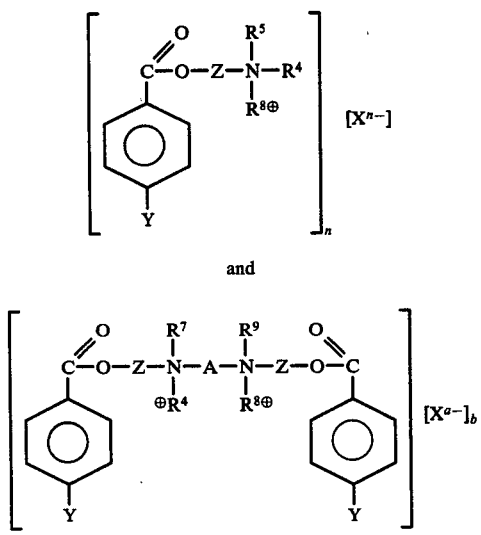

and

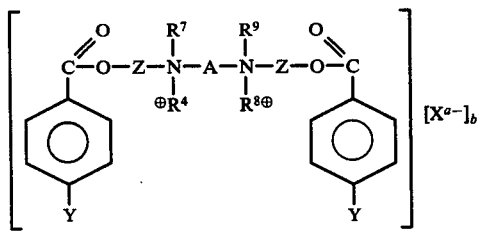

wherein Y is a dialkyl amino radical, Z is a bivalent hydrocarbon having from 1 to 5 carbon atoms, X is an anion radical and $n$, $a$ and $b$ are integers 1 or 2 and A represents a $C_1$-$C_{20}$ bivalent hydrocarbon radical.

Sunscreening compositions containing effective amounts of the above cationic aminobenzoates are capable of screening harmful ultraviolet radiation while permitting transmission of beneficial rays. In such a manner the individual user may subject himself to sunlight to cause the aesthetically desirable tanning of the skin while alleviating the problems of sunburn or erythema which is usually accompanied by discomfort and pain. The cosmetic compositions containing the cationic aminobenzoate material, when topically applied, form a material which adheres to the skin and resists removal therefrom when subjected to the action of fresh or salt water or through perspiration of the user. These compositions are, therefore, long lasting and need not be applied numerous times to insure proper protection.

DETAILED DESCRIPTION OF THE INVENTION

Sunscreening compositions containing at least one cationic aminobenzoate ester, as herein after described, in combination with a cosmetic carrier material have been found capable of screening harmful ultraviolet radiation while permitting transmission of the beneficial rays of the sun. In this manner, the individual may subject himself to sunlight or to an artificial ultraviolet radiation source, such as a sunlamp, to cause the aesthetically desired tanning of the skin while substantially eliminating the problems of sunburn and its accompanying discomfort and pain. Furthermore, it has been found that such sunscreening compositions containing at least one cationic aminobenzoate filtering compound are not easily removed from the skin by the action of fresh or salt water or through the perspiration of the user. Therefore, applications of these compositions are long lasting, do not have to be frequently applied, and form an advantageous cosmetic protective coating.

It has been found that dialkylaminobenzoic acid esters which contain a quaternary amine in the ester group are substantive sunscreening agents. These compounds may be selected from the groups represented by the following general formula:

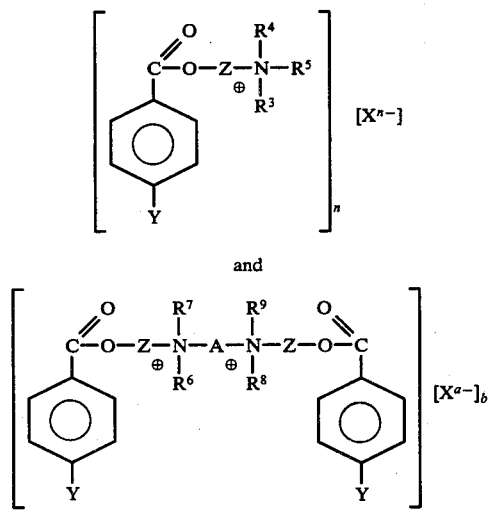

wherein Y represents amino radicals,

$R^1$ and $R^2$ in such amino radicals may be a $C_1$–$C_5$ alkyl group such as, methyl, ethyl, propyl and butyl, isobutyl n-pentyl, iso-pentyl, and the like; aryl groups such as, phenyl, tolyl and xenyl and the like groups; alkaryl groups, such as benzyl phenethyl, phenyl-n-propyl, phenylisopropyl, phenylisobutyl and the like and substituted alkyl, aryl and alkaryl groups wherein said substitution may be a halogen, hydroxy, alkoxy, carboxy, cyano and acyloxy. Specific examples of such substitution groups are chlorine, bromine, iodine, methoxy, ethoxy, hydroxyethyl, hydroxypropyl, hydroxybutyl, cyanomethyl, cyanoethyl, cyano-n-propyl, cyanoisopropyl, cyanobutyl and the like.

The ester group of the cationic aminobenzoates of the general formulae I and II described hereinabove contains a divalent hydrocarbon radical represented by Z. Z may be selected from any $C_1$–$C_5$ bivalent hydrocarbon such as methylene, ethylene, propylene, pentamethylene, and the like groups. Said bivalent hydrocarbon radical is covalently bonded to the carboxy group of the benzoic acid nucleus and the remaining valence is covalently bonded to a quaternary ammonium group.

The monoquaternary ammonium radical of formula I contains $R^3$ and $R^4$ substitution selected from the group consisting of alkyl, aryl and alkaryl groups similar to those described hereinabove of the pendent para amino group of the subject compounds. The monoquaternary ammonium radical also contains an $R^5$ substitution which is a $C_1$–$C_{20}$ alkyl group such as methyl, ethyl, n-propyl, isopropyl, pentyl, hexamethyl, dodecyl and the like groups.

The diquaternary ammonium radical, as represented by formula II above, contains $R^6$, $R^7$, $R^8$ and $R^9$ substitution groups selected from the group consisting of alkyl, aryl, and alkaryl radicals similar to those described hereinabove of the pendent para amino group of the subject compounds. The symbol A of formula II represents a bivalent $C_1$–$C_{20}$ hydrocarbon bridging radicals which can be exemplified by methylene, ethylene, trimethylene, tetra, penta, hexa, hepta, octa, nona, deca, trideca, heptadeca, nonadecamethylene, and the like as well as branched $C_1$–$C_{20}$ bivalent hydrocarbons such as ethylidene, propylidene, isopropylidene, butylidene and the like.

The cationic aminobenzoates represented by formulae I and II above which have been found useful as a substantive sunscreening material contain anions which form a neutral electron valence system. The symbol X represents useful anions, such as halogen anions including chloro, bromo, fluoro or iodo anion, sulfate, bisulfate, carbonate, bicarbonate, sulfite, bisulfite and the like. The symbol $n$ of formula I may be a whole integer 1 or 2 in such a manner as to form a substantially electron valence neutral material. When a monovalent anion, such as chloro, is used, the symbol $n$ equals 1 and when a bivalent anion, such as sulfate, is used, $n$ equals 2.

The symbols $a$ and $b$ of formula II may also be whole integers 1 or 2 in such a manner that a substantially electron valence neutral material is formed. When a monovalent anion, such as chloro, is used, the symbol $a$ will be 1 and the symbol $b$ will be 2. Similarly, when a divalent anion, such as sulfate, is used, the symbol $a$ will be 2 and $b$ will be 1.

The above described cationic aminobenzoate may be produced in any of the conventional manners, such as by the esterification of a paradialkyl aminobenzoic acid with a gamma (dialkylamino) alkanol. The thus formed ester may be further reacted with an alkyl halide or dihalide to form, respectively, the mono or diquaternary cationic compound.

Cationic benzoate esters which have been found highly effective as sunscreening agents with improved adherence to the skin may be exemplified by such monoquaternary compounds as quaternary alkyl procaine halides, such as quaternary dimethylprocaine methyl iodide, paradimethylaminobenzoyl diethylamino-2-hydroxypropanol methyl iodide and the like. Diquaternary compounds may be represented by diquaternary dimethyl procaine dialkyl dihalides, such as diquaternary dimethyl procaine dimethyl diiodide, diquaternary diethyl procaine dimethyl dichloride, methylimidazoline-2-hydroxy-3-ethyl-p-dimethylaminobenzoate dimethyl dichloride and the like.

The above described cationic aminobenzoates may be readily formulated into a cosmetic carrier material for application on the skin of the user prior to subjection to tanning rays, such as from natural or artificial sources. Such compositions should contain at least one of the cationic aminobenzoates but may, alternately, contain a mixture of more than one of the subject sunscreening agents. Such mixtures may be desirable to broaden the protected range against erythema forming ultraviolet rays.

It has been found that the cationic benzoate materials are effective sunscreening agents when used in concentrations of from about 1 part to 10 parts based on 100 parts of the total composition. In most instances it has been found preferable to use from about 2 part to about 8 parts of the cationic amino benzoate material based on 100 parts of total composition. An ultraviolet absorbing composition for personal use which is commercially acceptable must be capable of screening out at least 85% of the erythema causing rays. The desired result, as is well known by those skilled in the art, can be obtained by adjusting the percentage of the ultraviolet absorber material used. Therefore, the particular effective amount of aminobenzoate which will be necessary in any given composition will depend upon a particular aminobenzoate ester or group of esters used and such determination can be readily obtained by those skilled in the art.

The novel substantive sunscreening material described herein may be prepared into cosmetic sunscreening preparations by methods well known in the art. They may be associated with any suitable cosmetically acceptable vehicle to produce the desired cosmetic product. Thus, the cationic aminobenzoates may be dissolved in an aliphatic alcohol. These alcohols may be a $C_1-C_5$ lower alcohol or mixtures of two or more different alcohols. The alcohols may be any dermatologically acceptable material which will easily evaporate from the skin after application and in which the particular cationic aminobenzoate being used has some solubility. Such alcohols may be selected from methanol, ethanol, propanol, isopropanol and the like. These alcohols may be used alone or with polyols, such as ethylene glycol, 1,2-propanediol, 1,3-propanediol, 1,3-butanediol, diethylene glycol, triethylene glycol, glycerol and the like.

The novel sunscreening agent described herein may be contained in other suitable cosmetic carrier materials which may contain the cationic aminobenzoate or may be a mixture of a hydroalcoholic solution of the aminobenzoate in oily lotions, emulsified water-in-oil lotions, various creams and the like.

In addition, other of the usual components, such as perfumes, fillers, dyes, colorants, emulsifiers and the like may be added to the substantive sunscreening compositions described hereinabove. The type and amount of such additional components will depend on the factors of method of application, the condition of the skin of the user, and the like and are well known to those skilled in the art.

The sunscreening compositions, as described hereinabove, are applied to the skin in any convenient manner, such as by hand rubbing small amounts onto the exposed skin which is to be subjected to the suntan causing radiation. Alternately, the composition may be sprayed from an aerosol container onto the exposed skin. Such aerosol containers may contain, in addition to the cosmetic carrier materials, a propellant material, such as carbon dioxide, nitrous oxide, hydrocarbons and halogenated hydrocarbons, such as one of the chloro fluoro hydrocarbons, which are well known as Freon materials. The composition, when applied over the skin of the body, will contain the cationic aminobenzoates described hereinabove which are resistant to removal by the abrasive action of fresh or salt water or through the perspiration of the user and, therefore, will form a substantive material which will effectively protect the skin from erythema-causing rays.

EXAMPLE I

Aqueous alcoholic compositions for use as a skin protecting sunscreening composition are prepared by incorporating five parts of the following cationic benzoate esters into 100 parts of aqueous alcoholic medium containing 30 parts water and 70 parts of isopropanol:

p-aminobenzoyldiethylaminoethanol ethyl iodide
p-aminobenzoyldiethylaminoethanol methyl iodide
p-dimethylaminobenzoyldiethylaminoethanol ethyl iodide
p-dimethylaminobenzoyldiethylaminoethanol ethyl chloride
p-diethylaminobenzoyldiethylaminopropanol methyl iodide
p-diethylaminobenzoyldimethylaminopropanol methyl iodide
p-diethylaminobenzoyldiphenylaminopropanol methyl iodide
p-dimethylaminobenzoyldiethylaminoethanol quaternized with ethyl diiodide
p-dimethylaminobenzoyldiethylaminoethanol quaternized with octyl dichloride
p-diethylaminobenzoyldiethylaminopropanol quaternized with methyl diiodide
p-diethylaminobenzoyldiphenylaminopropanol quaternized with methyl dichloride The compositions are applied to the skin of several subjects and the treated areas exposed to ultraviolet rays (Xenon-arc-solar simulator) for time periods equivalent to from 2 to 6 times a previously established minimum erythemal dose for each volunteer. Substantially no erythema is observed at the treated sites over a 24 hour period.

EXAMPLE II

Samples of various cationic sunscreening compounds, as listed in Table I below, were tested for their substantive properties. Swatches of natural blond hair were cut into ¼-½ inch long clippings. Each 20 gram hair batch was washed once with 1,000 ml. of a 1% sodium bicarbonate solution by stirring vigorously for about 2 hours and then leaving it soak overnight. The sodium bicarbonate wash was then decanted and the hair was given six consecutive rinses with 2500 ml. portions of deionized water by stirring vigorously for 10 minutes, settling for 15 to 20 minutes and then decanting. The sixth water rinse gave 97.5–99% light transmission in the 280–320 μ. range determined with a Bausch & Lomb Spectronic 505 spectrophotometer. After decantation of the sixth water rinse, the hair was transferred to a buchner funnel, broken up into small clumps or mats, and allowed to drain overnight. The bulk of the remaining surface water was removed by pressing the hair mats between paper towels. The last trace of surface water was removed by mechanically breaking down the hair mats into the individual fibers and blotting dry between sheets of filter paper. The hair was further dried with a hair dryer and stored in a screwcapped glass jar until used.

The standard procedure used was to soak 0.1 gram samples of hair clippings conditioned, as described above, in a 10 ml. portion of a solution of the cationic substantive sunscreening agent in buffer and in a 10 ml. portion of the corresponding buffer for a period of exactly 30 minutes. The solution and the buffer were then pipetted off of the hair samples and diluted with the original buffer. The solution was diluted to an appropriate concentration for ultraviolet light absorption measurement and the buffer was diluted in the same proportion as the solution. UV absorption measurements were run on the diluted solution and on an equivalent dilution of the original solution of the substantive agent with the buffer using a Bausch & Lomb Spectronic 505 spectrophotometer in the 250-350 mµ range. The absorption curves continuously record the optical density (O.D.) of the solution which is directly proportional to the amount of ultraviolet absorption at increasing wavelengths. The UV absorption by the solution of a material is directly proportional to the concentration. Pick up of the substantive agent by the hair lowers the concentration of the material in the solution resulting in a proportionate decrease in the O.D. The amount of a substantive material picked up by the hair was calculated from the decrease in O.D. at the maximum absorption wavelength resulting from contact with the hair corrected by the increase in O.D. of the corresponding buffer solution due to contact with the hair for the same length of time.

The substantive character of the novel sunscreening materials of the present invention shows a capability of providing adequate adhesion to keratin material of human origin, hair, as made manifest by the data of Table I. In comparison, Escalol 506 which is a proprietary name for amyl paradimethylaminobenzoate showed no uptake when tested in the same manner. Each of the quaternary dialkyl aminobenzoates showed good uptake even at the low concentrations tested.

Each of the hair samples prepared were water-washed after obtaining equilibrium with the sunscreening solution to check for possible leaching of sunscreening agent by water. No significant leaching was found with any of the quaternary ammonium compounds tested.

| Compound | Concentration | Carrier | Initial Abs. Max (mu) | Final Abs. Max (mu) | initial O.D. | Final O.D. | Indicated Uptake |
| --- | --- | --- | --- | --- | --- | --- | --- |
| Dimethyl procaine quaternarized w. decyl bromide | 0.01 g/l | 50/50 ethanol/water | 320 | 319 | 0.63 | 0.52 | 17.5% |
| Dimethyl procaine quaternarized w. dodecyl bromide | 0.01 g/l | 50/50 ethanol/water | 320 | 319 | 0.60 | 0.47 | 21.7% |
| Dimethyl procaine quaternarized w. hexadecyl bromide | 0.01 g/l | 50/50 ethanol/water | 319 | 318 | 0.49 | 0.34 | 30.6% |
| Dimethyl procaine quaternarized w. octadecyl bromide | 0.01 g/l | 50/50 ethanol/water | 319 | 320 | 0.47 | 0.31 | 34.0% |
| Dimethyl procaine quaternarized w. decyl dibromide | 0.01 g/l | 50/50 isopropanol/water | 319 | 319 | 0.57 | 0.18 | 68.4% |

EXAMPLE III

Ninety-five (95) parts of an aqueous alcoholic solution containing 30 parts water and 70 parts ethanol is mixed with 5 parts of a compound having the formula:

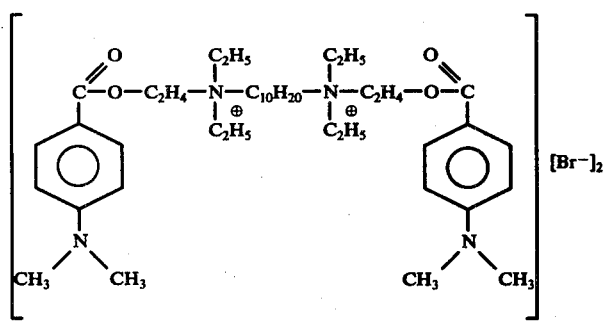

The solution was tested in the same manner as that described in Example II above. The sample showed good uptake of the substantive sunscreening agent on the in vitro hair sample. The hair sample was water washed after obtaining equilibrium with the sunscreening solution to check its substantivity quality against leaching by water. No significant leaching was found with this compound.

It will be understood that it is intended to cover all changes and modifications of the examples of the invention herein chosen for the purpose of illustration which do not constitute departures from the spirit and scope of the invention.

What is claimed is:

1. A method of protecting human skin from erythema producing ultraviolet radiation which comprises applying to said skin a composition of a cosmetic carrier containing from about 1-10 percent by weight based on the total weight of the composition of a cationic aminobenzoate having the general formula:

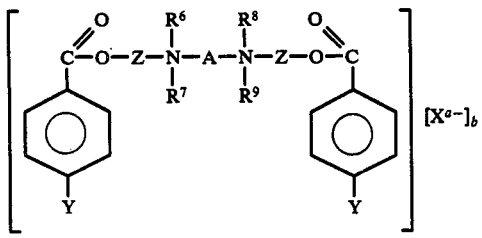

wherein Y is a amino radical having the formula

such that $R^1$ and $R^2$ are each selected from the group consisting of $C_1$–$C_5$ alkyl, aryl, alkaryl, substituted alkyl, substituted aryl, and substituted alkaryl; wherein Z is a bivalent alkyl hydrocarbon containing from 1 to 5 carbon atoms; wherein X is an anion selected from the group consisting of chloro, bromo, fluoro, iodo, sulfate, bisulfate, carbonate, bicarbonate, sulfite, and bisulfite; wherein $R^6$, $R^7$, $R^8$ and $R^9$ are selected from the group consisting of alkyl, aryl, and alkaryl; wherein A is a bivalent $C_1$–$C_{20}$ hydrocarbon bridging radical and wherein $a$ and $b$ are the integers 1 or 2.

2. The method of protecting the human skin according to claim 1 wherein the cosmetic carrier is an aliphatic alcohol containing from 1 to 5 carbon atoms.

3. The method according to claim 2 wherein the carrier is a hydroalcoholic solution of the aminobenzoate mixed with a carrier selected from the group consisting of oils, water-in-oil emulsions and creams.

4. The method according to claim 1 wherein the cationic benzoate composition is applied from an aerosol container.

5. The composition for providing longlasting protection to the human skin from erythema-causing ultraviolet radiation which comprises a cosmetic carrier material containing distributed therein from about 1 percent to about 10 percent based on the total weight of the composition of a cationic aminobenzoate having the general formula:

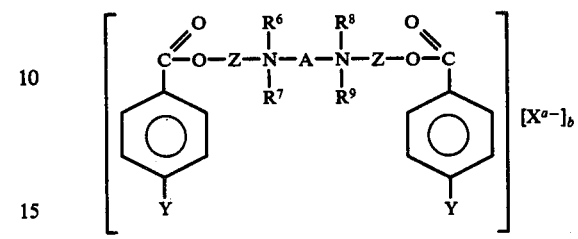

wherein Y is a amino radical having the formula of

such that $R^1$ and $R^2$ are each selected from the group consisting of $C_1$–$C_5$ alkyl, aryl, alkaryl, substituted alkyl, substituted aryl and substituted alkaryl; wherein Z is a bivalent alkyl hydrocarbon containing from 1 to 5 carbon atoms; wherein X is an anion selected from the group consisting of chloro, bromo, fluoro, iodo, sulfate, bisulfate, carbonate, bicarbonate, sulfite, and bisulfite; wherein $R^6$, $R^7$, $R^8$, and $R^9$ are selected from the group consisting of alkyl, aryl, and alkaryl; wherein A is a bivalent $C_1$–$C_{20}$ alkyl hydrocarbon bridging radical and wherein $a$ and $b$ are integers 1 or 2.

6. The composition according to claim 5 wherein the carrier material contains an aliphatic alcohol containing from 1 to 5 carbon atoms.

7. A composition according to claim 5 wherein the carrier material contains an aerosol propellant material.

* * * * *